United States Patent [19]

Wilder

[11] 4,301,260
[45] Nov. 17, 1981

[54] VULCANIZABLE RUBBER COMPOSITIONS SCORCH INHIBITED BY 2-(THIOAMINO)-4,6-DIAMINO-1,3,5-TRIAZINES

[75] Inventor: Gene R. Wilder, Medina, Ohio

[73] Assignee: Monsanto Company, St. Louis, Mo.

[21] Appl. No.: 148,061

[22] Filed: May 12, 1980

[51] Int. Cl.³ .................. C08C 19/20; C08C 19/22
[52] U.S. Cl. ............................ 525/348; 260/791; 525/333; 544/199
[58] Field of Search ............... 525/332, 334, 333, 348; 260/791, 720; 544/199

[56] References Cited

U.S. PATENT DOCUMENTS 3,801,537  4/1974  Westlinning .................. 260/42.33

Primary Examiner—C. A. Henderson
Attorney, Agent, or Firm—Larry R. Swaney

[57] ABSTRACT

Vulcanizable rubber compositions inhibited from premature vulcanization by 2-(thioamino)-4,6-diamino-1,3,5-triazines are described.

9 Claims, No Drawings

VULCANIZABLE RUBBER COMPOSITIONS SCORCH INHIBITED BY 2-(THIOAMINO)-4,6-DIAMINO-1,3,5-TRIAZINES

This invention relates to improved vulcanizable rubber compositions inhibited from premature vulcanization, to a process for inhibiting premature vulcanization of rubber, and to compounds which are potent premature vulcanization inhibitors.

BACKGROUND OF THE INVENTION

Vulcanization accelerators promote vulcanization of rubber by increasing the rate of vulcanization. Premature vulcanization inhibitors delay the onset of vulcanization which inhibition extends the processing time vulcanizable rubber compositions may be handled without scorching the batch and extends the time such compositions may be stored without serious deterioration.

The use of (aminothio)-triazines as accelerators for vulcanization of rubber is known, U.S. Pat. Nos. 3,366,598, 3,655,599, and 3,844,970.

SUMMARY OF THE INVENTION

It has now been discovered that (thioamino)-triazines are premature vulcanization inhibitors. Surprisingly, reversal of the respective positions of the sulfur and nitrogen atoms in respect to the triazine ring has a significant effect upon the vulcanization activity of the compounds. Triazines having aminothio substituents are accelerators, whereas, triazines having thioamino substituents are premature vulcanization inhibitors. Improved vulcanizable rubber compositions of the invention comprise sulfur-vulcanizable rubber, sulfur-vulcanizing agent, organic vulcanization accelerating agent, and, in an amount effective to inhibit premature vulcanization, a compound of the formula

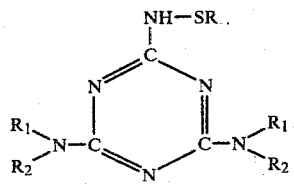

in which R, $R_1$ and $R_2$ independently are $C_1$–$C_{12}$ alkyl, $C_5$–$C_{12}$ cycloalkyl, $C_7$–$C_{10}$ aralkyl, phenyl, or mono- or di-substituted phenyl wherein the substituents are $C_1$–$C_6$ alkyl, $C_1$–$C_6$ alkoxy, or $C_1$–$C_6$ alkylthio, or $R_1$ is hydrogen.

Inhibitors of the invention are prepared by reacting the appropriate sulfenyl chloride with 2-amino-4,6-di-(substituted amino)-1,3,5-triazine in the presence of a hydrogen chloride acceptor. Alternatively, sulfenyl chloride is reacted with an alkali metal salt of 2-amino-4,6-di-(substituted amino)-1,3,5-triazine.

Examples of satisfactory radicals for R, $R_1$ and $R_2$ are methyl, ethyl, propyl, isopropyl, n-butyl, sec-butyl, isobutyl, t-butyl, pentyl, hexyl, heptyl, octyl, t-octyl(1,1,3,3 tetramethylbutyl), nonyl, decyl, dodecyl, cyclohexyl, 4-methylcyclohexyl, 2-methylcyclohexyl, cycloheptyl, cyclopentyl, cyclooctyl, cyclodecyl, cyclododecyl, phenyl, benzyl, α-methylbenzyl, α,α-dimethylbenzyl, phenethyl, 3-phenylpropyl, 4-phenylbutyl, 2-methylphenyl, 3-methylphenyl, 4-methylphenyl, 2,4-dimethylphenyl, 4-t-butylphenyl, 4-ethoxyphenyl, 4-methoxyphenyl, 4-(methylthio)phenyl and 2-ethyl-4-butylphenyl.

In preferred compounds of the invention, R is $C_5$–$C_8$ cycloalkyl peferably cyclohexyl, or secondary $C_3$–$C_8$ alkyl, $R_1$ is hydrogen or $C_1$–$C_6$ alkyl and $R_2$ is $C_1$–$C_6$ alkyl.

Illustrative examples of inhibitors of the invention are:

2-(methylthioamino)-4,6-di(t-butylamino)-1,3,5-triazine
2-(ethylthioamino)-4,6-di(t-butylamino)-1,3,5-triazine
2-(isopropylthioamino)-4,6-di(t-butylamino)-1,3,5-triazine
2-(hexylthioamino)-4,6-di(t-butylamino)-1,3,5-triazine
2-(phenylthioamino)-4,6-di(t-butylamino)-1,3,5-triazine
2-(cyclopentylthioamino)-4,6-di(t-butylamino)-1,3,5-triazine
2-(cyclooctylthioamino)-4,6-di(t-butylamino)-1,3,5-triazine
2-(benzylthioamino)-4,6-di(t-butylamino)-1,3,5-triazine
2-(2-methylphenylthioamino)-4,6-di(t-butylamino)-1,3,5-triazine
2-(α-methylbenzylthioamino)-4,6-di(t-butylamino)-1,3,5-triazine
2-(α,α-dimethylbenzylthioamino)-4,6-di-(t-butylamino)-1,3,5-triazine
2-(4-methoxyphenylthioamino)-4,6-di(t-butylamino)-1,3,5-triazine
2-(cyclohexylthioamino)-4,6-di(methylamino)-1,3,5-triazine
2-(isopropylthioamino)-4,6-di(methylamino)-1,3,5-triazine
2-(phenylthioamino)-4,6-di(methylamino)-1,3,5-triazine
2-(benzylthioamino)-4,6-di(dimethylamino)-1,3,5-triazine
2-(cyclohexylthioamino)-4,6-di(dimethylamino)-1,3,5-triazine
2-(isopropylthioamino)-4,6-di(dimethylamino)-1,3,5-triazine
2-(phenylthioamino)-4,6-di(dimethylamino)-1,3,5-triazine
2-(benzylthioamino)-4,6-di(dimethylamino)-1,3,5-triazine
2-(cyclohexylthioamino)-4,6-di(ethylamino)-1,3,5-triazine
2-(isopropylthioamino)-4,6-di(ethylamino)-1,3,5-triazine
2-(phenylthioamino)-4,6-di(ethylamino)-1,3,5-triazine
2-(benzylthioamino)-4,6-di(ethylamino)-1,3,5-triazine
2-(cyclohexylthioamino)-4,6-di(phenylamino)-1,3,5-triazine
2-(isopropylthioamino)-4,6-di(phenylamino)-1,3,5-triazine
2-(phenylthioamino)-4,6-di(phenylamino)-1,3,5-triazine
2-(benzylthioamino)-4,6-di(phenylamino)-1,3,5-triazine
2-(cyclohexylthioamino)-4,6-di(cyclohexylamino)-1,3,5-triazine
2-(isopropylthioamino)-4,6-di(cyclohexylamino)-1,3,5-triazine
2-(phenylthioamino)-4,6-di(cyclohexylamino)-1,3,5-triazine
2-(benzylthioamino)-4,6-di(cyclohexylamino)-1,3,5-triazine The inhibitors of the invention are incorporated into rubber stocks by mixing on a mill or in an internal mixer such as a Banbury mixer. However, the inhibitors may be incorporated by addition to latex, if desired. The process of the invention is particularly applicable to sulfur-vulcanizable rubber compositions which rubber compositions contain a sulfur vulcanizing agent such as an amine disulfide or a polymeric polysulfide but preferably, the vulcanizing agent is elemental sulfur (usually about 0.5-5 parts by weight of sulfur are used per 100 parts by weight of rubber). Rubber compositions containing organic accelerating agents are particularly improved by the inhibitors of the invention. Any organic accelerating agents in an amount effective to accelerate the sulfur vulcanization of rubber is satisfactory in the practice of this invention. Accelerating effective amounts are generally within the range of 0.1-5.0 parts by weight accelerator per 100 parts by weight rubber. Examples of suitable accelerators are described in U.S. Pat. No. 3,546,185, Column 9, lines 53-75 and in U.S. Pat. No. 3,780,001, Column 4, lines 43-72. The process of the invention is applicable to a wide variety of natural and synthetic rubbers and mixtures thereof and especially applicable to diene rubbers. Examples of satisfactory rubbers are described in U.S. Pat. No. 3,546,185, Column 10, lines 15-21 and U.S. Pat. No. 3,780,001, Column 5, lines 5-33. The vulcanizable composition may also contain conventional compounding ingredients such as reinforcing pigments, extenders, processing oils, antidegradants and the like.

Small amounts of inhibitors are effective to inhibit premature vulcanization. Improvements in processing safety may be observed with 0.05 parts or less of inhibitor per 100 parts rubber. Although there is no upper limit in the amount of inhibitor used, generally the amount does not exceed 5 parts inhibitor per 100 parts rubber. Typically, the amount of inhibitor added is about 0.1 to 2.5 parts per 100 parts rubber with amounts of about 0.2 to 1 part inhibitor per 100 parts rubber being commonly used. Methods for determining scorch times and curing characteristics of rubber stocks used in demonstrating this invention are described in U.S. Pat. No. 3,546,185, Column 13, lines 30-53.

PREFERRED EMBODIMENTS

The compounds of the invention are prepared by causing to react a sulfenyl chloride and an alkali metal salt of an amino-1,3,5-triazine. The by-products and product are separated and purified by conventional procedures. The alkali metal salt intermediate is prepared by causing to react amino-s-triazine and alkali metal alcoholate in an inert medium and removing the alcohol by-product by distillation. A satisfactory process for preparing compounds of the invention is illustrated below.

EXAMPLE 1

Cyclohexane sulfenyl chloride (0.13m) solution in 80 grams of benzene is added dropwise at 60° C. over a twenty minute period to 2-sodium amino-4,6-di(t-butylamino)-1,3,5-triazine in 200 grams of benzene. Salt by-product is removed by washing with water. The benzene is removed by evaporation and heptane is added to crystallize the product. 2-(Cyclohexylthioamino)-4,6-di(t-butylamino)-1,3,5-triazine, m.p. 186° C., is recovered. Identification of product is confirmed by NMR spectral analysis.

The process of the invention is demonstrated by incorporating inhibitors into portions of rubber stocks comprising the ingredients shown in Table 1. All parts are by weight.

TABLE 1

| STOCK | 1 | 2 | 3 |
| --- | --- | --- | --- |
| Natural Rubber | 100 | 100 | 100 |
| Carbon Black | 40 | 40 | 40 |
| Processing Oil | 10 | 10 | 10 |
| Hydrocarbon Wax | 2 | 2 | 2 |
| Zinc Oxide | 5 | 5 | 5 |
| Stearic Acid | 1 | 1 | 1 |
| Sulfur | 2.5 | 2.5 | 2.5 |
| N-(t-butyl)-2-benzothiazole sulfenamide | 0.6 | 0.6 | 0.6 |
| N-(cyclohexyl)-4,6-bis-(t-butylamino)-1,3,5-triazine-2-sulfenamide | — | 0.4 | — |
| 2-(cyclohexylthioamino)-4,6-bis-t(butylamino)-1,3,5-triazine | — | — | 0.4 |
| Mooney Scorch @ 121° C. | | | |
| t5 | 42.3 | 54.9 | 78.8 |
| % increase in scorch delay | — | 30 | 63 |
| Stress-Strain @ 153° C. | | | |
| UTS, MPa | 25.2 | 27.0 | 26.1 |
| $M_{300}$, MPa | 9.3 | 12.3 | 9.9 |
| Elong., % | 580 | 510 | 550 |

Stock 1 is a control. Stock 2 contains a prior art compound in which the sulfenamide sulfur atom is attached directly to the triazine ring. Stock 3 contains an inhibitor of the invention which only differs from the prior art compound by the relative positions of the sulfur and nitrogen atoms, i.e., the sulfenamide nitrogen atom is attached directly to the triazine ring. The data show that surprisingly the inhibitor of the invention, Stock 3, is twice as potent as a prevulcanization inhibitor than the corresponding prior art compound. The compound of Stock 3 increases scorch delay 63% versus only 30% for the compound of Stock 2. The data also show that the other properties of the vulcanizate containing 2-(cyclohexylthioamino)-4,6-bis(t-butylamino)-1,3-triazine are essentially the same as the control containing no additive. It is significant that the known compound of Stock 2 causes an increase in modulus, $M_{300}$, whereas, the inhibitor of the invention has little, if any, effect upon modulus.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. A composition comprising sulfur-vulcanizable diene rubber, sulfur-vulcanizing agent, organic vulcanization accelerating agent, and, in an amount effective to inhibit premature vulcanization, a compound of the formula

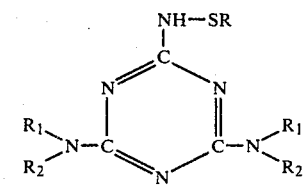

in which R, $R_1$ and $R_2$ independently are $C_1$-$C_{12}$ alkyl, $C_5$-$C_{12}$ cycloalkyl, $C_7$-$C_{10}$ aralkyl, phenyl, or mono- or di-substituted phenyl wherein the substituents are $C_1$–$C_6$ alkyl, $C_1$–$C_6$ alkoxy, or $C_1$–$C_6$ alkylthio, or $R_1$ is hydrogen.

2. The composition of claim 1 in which the vulcanizing agent is elemental sulfur and the rubber is a diene rubber.

3. The composition of claim 2 in which R is $C_1$–$C_6$ alkyl, $C_5$–$C_8$ cycloalkyl, benzyl, or phenyl.

4. The composition of claim 3 in which $R_2$ is $C_1$–$C_6$ alkyl.

5. The composition of claim 4 in which $R_1$ is hydrogen.

6. The composition of claim 4 in which $R_1$ is $C_1$–$C_6$ alkyl.

7. The composition of claim 5 in which R is cyclohexyl.

8. The composition of claim 7 in which $R_2$ is t-butyl.

9. The composition of claim 3 comprising a benzothiazole or thiuram accelerator.

* * * * *